(12) United States Patent
Duranti et al.

(10) Patent No.: US 8,257,758 B2
(45) Date of Patent: *Sep. 4, 2012

(54) PROCESS FOR THE EXTRACTION, PURIFICATION AND ENZYMATIC MODIFICATION OF SOY 7S GLOBULIN ALPHA' SUBUNIT FOR USE AS HYPOCHOLESTEROLEMIZING AGENT

(75) Inventors: Marcello Duranti, Milan (IT); Paolo Morazzoni, Milan (IT)

(73) Assignee: Indena S.p.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/013,966

(22) Filed: Jan. 26, 2011

(65) Prior Publication Data

US 2011/0118182 A1 May 19, 2011

Related U.S. Application Data

(62) Division of application No. 12/104,473, filed on Apr. 17, 2008, now Pat. No. 7,901,718, which is a division of application No. 10/502,582, filed as application No. PCT/EP03/00798 on Jan. 27, 2003, now Pat. No. 7,465,467.

(30) Foreign Application Priority Data

Jan. 29, 2002 (IT) .............................. MI2002A0147

(51) Int. Cl.
*A61K 36/48* (2006.01)
(52) U.S. Cl. ..................................................... 424/757
(58) Field of Classification Search .................. None
See application file for complete search history.

(56) References Cited

U.S. PATENT DOCUMENTS

| | | | |
|---|---|---|---|
| 4,409,248 A | 10/1983 | Lehnhardt et al. | |
| 6,171,640 B1 | 1/2001 | Bringe | |
| 6,365,802 B2 | 4/2002 | Kridl | |
| 6,541,259 B1 | 4/2003 | Lassner et al. | |
| 2001/0011377 A1 | 8/2001 | Kinney et al. | |
| 2001/0024677 A1 | 9/2001 | Bringe | |
| 2005/0089934 A1* | 4/2005 | Ishimaru et al. | 435/7.1 |
| 2005/0214346 A1 | 9/2005 | Bringe et al. | |
| 2006/0159826 A1* | 7/2006 | Wong | 426/590 |

FOREIGN PATENT DOCUMENTS

| | | |
|---|---|---|
| EP | 0 797 928 | 10/1997 |
| EP | 1 172 087 | 1/2002 |
| FR | 2 784 029 | 4/2000 |
| WO | 00/77034 | 12/2000 |

OTHER PUBLICATIONS

Wu et al., "Pilot-plant fractionation of soybean glycinin and beta-conglycinin." Journal of the American Oil Chemists' Society, vol. 76, No. 3, 1999, pp. 285-293, XP002243567.
Lovati et al. "Soy protein peptides regulate cholesterol homeostasis in Hep G2 cells." Journal of Nutrition, vol. 130, No. 10, Oct. 2000 pp. 2543-2549, XP002243172 ISSN: 0022-3166.
Lovati et al. "Soybean protein products as regulators of liver low-density lipoprotein receptors I. indentification of active betta-conglycinin subunits" Journal of Agricultural and Food Chemistry, American Chemical Society, Washington, US, vol. 46, No. 7, 1998, pp. 2474-2480, XP002928070 ISSN: 0021-8561.
Manzoni et al. "Soybean protein products as regulators of liver low-density lipoprotein receptors. II. alpha alpha su rich commercial soy concentrate and alpha su defficient mutant differently affect low-density lipoprotein receptor activation." Journal of Agricultural and Food Chemistry, vol. 46, No. 7, 1998, pp. 2481-2484, XP002243568.
Database WPI, Section Ch, Week 199433 Derwent Publications Ltd., London, GB; AN 1994-268692 XP 002243569 & JP 06 197788 (Fuji Seiyu KK), Jul. 19, 1994.

* cited by examiner

Primary Examiner — Christopher R. Tate
Assistant Examiner — Deborah A. Davis
(74) Attorney, Agent, or Firm — Young & Thompson

(57) ABSTRACT

A purified amino-terminal polypeptide fragment of the soy β-conglycinin α' subunit is prepared by selective extraction of defatted soy with an aqueous solution of sodium bisulfite, precipitation with ethanol, and Metal Affinity Chromatography (MAC) under denaturing conditions to obtain the α' subunit. The α' subunit is then enzymatically treated with chymotrypsin and subjected to further MAC to recover the amino-terminal fragment of the polypeptide (MW 28,000 Da).

7 Claims, 2 Drawing Sheets

β-CONGLYCININ ENRICHMENT

α' SUBUNIT

PROCESS FOR THE EXTRACTION, PURIFICATION AND ENZYMATIC MODIFICATION OF SOY 7S GLOBULIN ALPHA' SUBUNIT FOR USE AS HYPOCHOLESTEROLEMIZING AGENT

CROSS REFERENCE TO RELATED APPLICATIONS

This application is a new divisional application of application Ser. No. 12/104,473 filed Apr. 17, 2008, which is a divisional of application Ser. No. 10/502,582 filed Feb. 7, 2005 (now U.S. Pat. No. 7,465,467), which is a 371 National Stage application of PCT/EP03/00798 filed Jan. 27, 2003, which claims priority to Italian Application No. MI2002A000147 filed on Jan. 29, 2002. The entire contents of each of the above-identified applications are hereby incorporated by reference.

FIELD OF THE INVENTION

The present invention relates to a process for the extraction, purification and enzymatic modification of β-conglycinin α' subunit.

According to the invention, β-conglycinin is selectively extracted from ground, defatted soy, then precipitated by treatment with aqueous ethanol; the enriched fraction is then subjected to Metal Affinity Chromatography (MAC) in denaturant conditions to obtain the α' subunit. The latter is treated with chymotrypsin, then subjected to a further affinity chromatography step to recover the amino-terminal region of this polypeptide (MW 28,000 Da).

TECHNICAL BACKGROUND

The known cholesterol lowering properties of soy and derivatives thereof are related with the content in isoflavones (Kirk et al., 1998) and in proteins (Anderson et. al, 1995).

Soy proteins mainly consist of glycinins (11S fraction) and β-conglycinins (7S fraction), the latter consisting of three subunits, named α, α' and β (Thanh and Shibasaki, 1976). Studies carried out on soy proteins have established that the 7S fraction (Lovati et. al, 1992, 1996), particularly the α' subunit (Manzoni et. al, 1998) is capable of activating LDL receptor and is therefore the main responsible for the reduction of cholesterol plasma levels. In fact, treatment of an hepatic cell line with 7S globulin induces extensive degradation of the α and α' subunits and stimulation of LDL receptor activity, whereas β subunits are not degraded and the receptor is not activated. Moreover, soy mutants in which 7S fraction lacks α' subunit are not able to modify the receptor activity, even at high concentrations.

As a consequence of these experimental observations, methods are needed to obtain β-conglycinin in the pure form, as well as recovering and purifying the α' subunit, from which specific amino acidic sequences could subsequently be obtained by enzymatic treatment, without making use of peptide synthesis.

The process suggested by Than et al. (1975 and 1976) and subsequently modified by O'Keefe et al. (1991) allows to separate glycinins and β-conglycinins based on their different solubilities at different pH; however, cross-contamination is still high and gel filtration or affinity chromatography are required, which are costly and difficult to carry out on an industrial scale. Also the modification suggested by Nagano et al. (1992), although allowing to increase the fractions purity, is still an expensive method which can be used only on laboratory scale.

Recently, Wu et al. (1999) have described a method for separating glycinins and conglycinins on a pilot-plant scale. Glycinins are precipitated by two subsequent aqueous extractions at pH 8.5, followed by treatment of the supernatant with a 0.98 g/L bisulfite solution, while conglycinins are precipitated by adding 0.25 M NaCl to the mother liquors from the glycinins precipitation, then adjusting pH to 4.8. The process allows to treat high amounts of starting material and also provides high yields in protein, but the fractions purity is still unsatisfactory; β-conglycinin, in particular, undergoes degradation, apparently during diafiltration with water, which is a treatment necessary to reduce the bisulfite ions excess and to remove salts.

The above cited methods not only do not yield pure β-conglycinin, but above all do not envisage separation and purification of the α' subunit.

BRIEF SUMMARY OF THE INVENTION

According to the invention, a solid fraction enriched in β-conglycinin is prepared by extracting a defatted ground soy in an aqueous medium according to conventional procedures and subsequently precipitating the supernatant with aqueous ethanol; the resulting fraction is then purified by Metal Affinity Chromatography (MAC) in denaturant conditions to yield the pure α' subunit, which is subjected to enzymatic treatment with chymotrypsin to obtain the amino-terminal region which has apparently the highest LDL receptor-activating activity.

DETAILED DISCLOSURE OF THE INVENTION

Figure 1:
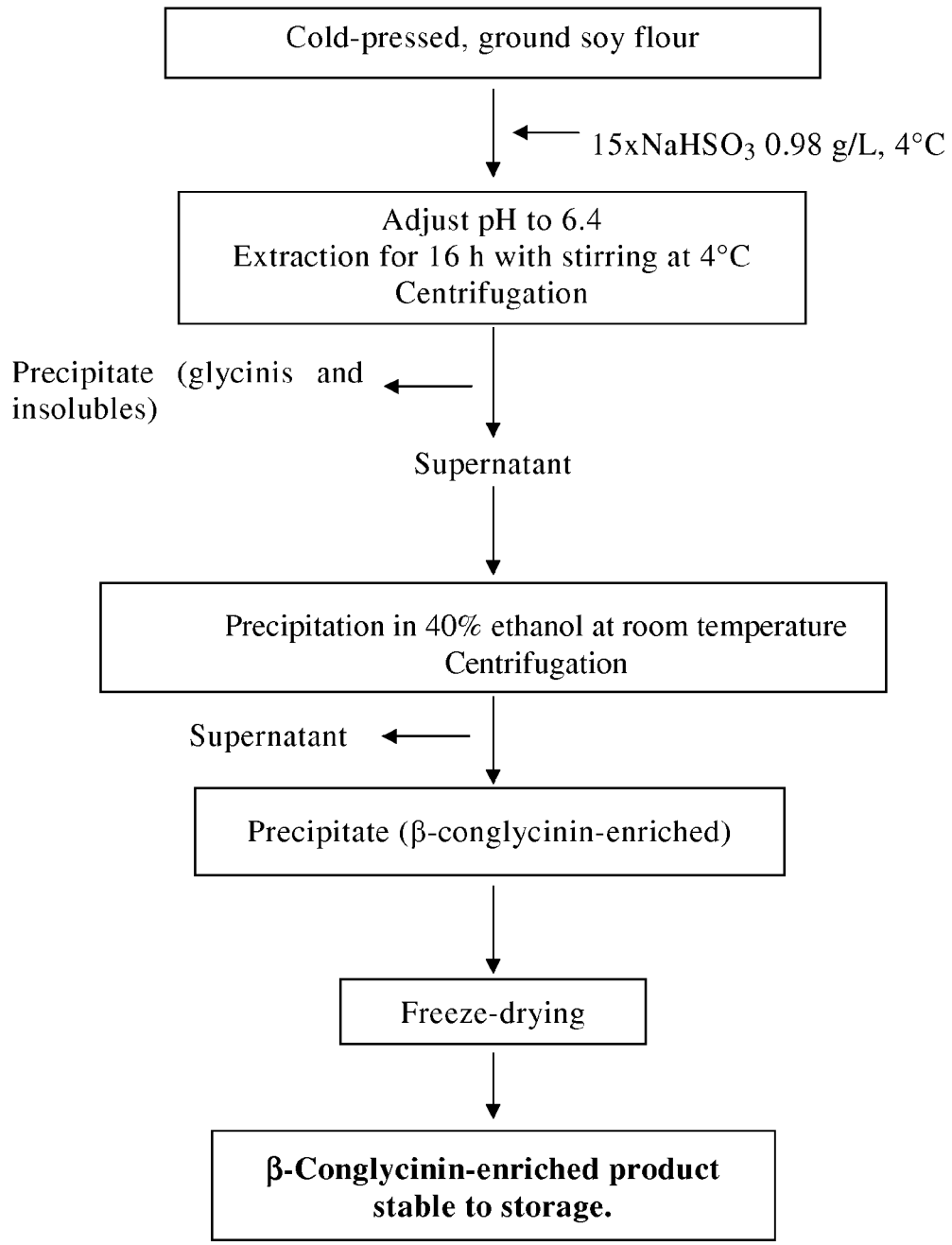
FIG. 1 is a flowchart showing an exemplary process of β-conglycinin enrichment.

The present invention relates to a process for the selective extraction, purification and enzymatic modification of soy β-conglycinin α' subunit, which process comprises the following steps:

a) extraction of a defatted ground soy with a sodium bisulfite aqueous solution at slightly acidic pH to obtain a β-conglycinin-enriched soluble protein fraction;

b) precipitation of the β-conglycinin fraction from step a) by treatment with ethanol;

c) purification of the precipitated fraction from step b) by Metal Affinity Chromatography (MAC) under denaturant conditions, to isolate the α' subunit;

d) enzymatic treatment of the α' subunit from step c) with a proteolytic enzyme and further purification by MAC chromatography;

e) precipitation of the α' subunit with organic solvents.

β-Conglycinin is enriched as shown in FIG. 1. The starting material is soy flour, defatted by removing the lipid fraction with solvents. The material is extracted with a sodium bisulfite aqueous solution at slightly acidic pH. A solution volume ranging from 14 to 16 times the weight of the starting material, preferably from 14.5 to 15.5 times, is used. The bisulfite concentration ranges from 0.80 to 1.20 g/L, preferably from 0.90 to 1.10 g/L, most preferably from 0.95 to 1.05 g/L. The extraction is carried out for a time ranging between 14 and 18 hours at a temperature ranging from −2 to 8° C. According to a preferred embodiment of the invention, the extraction is carried out for 16 hours with 15 volumes of a 0.98 g/L bisulfite solution at pH 6.4, at temperatures ranging from 0 to 4° C.

Figure 2:
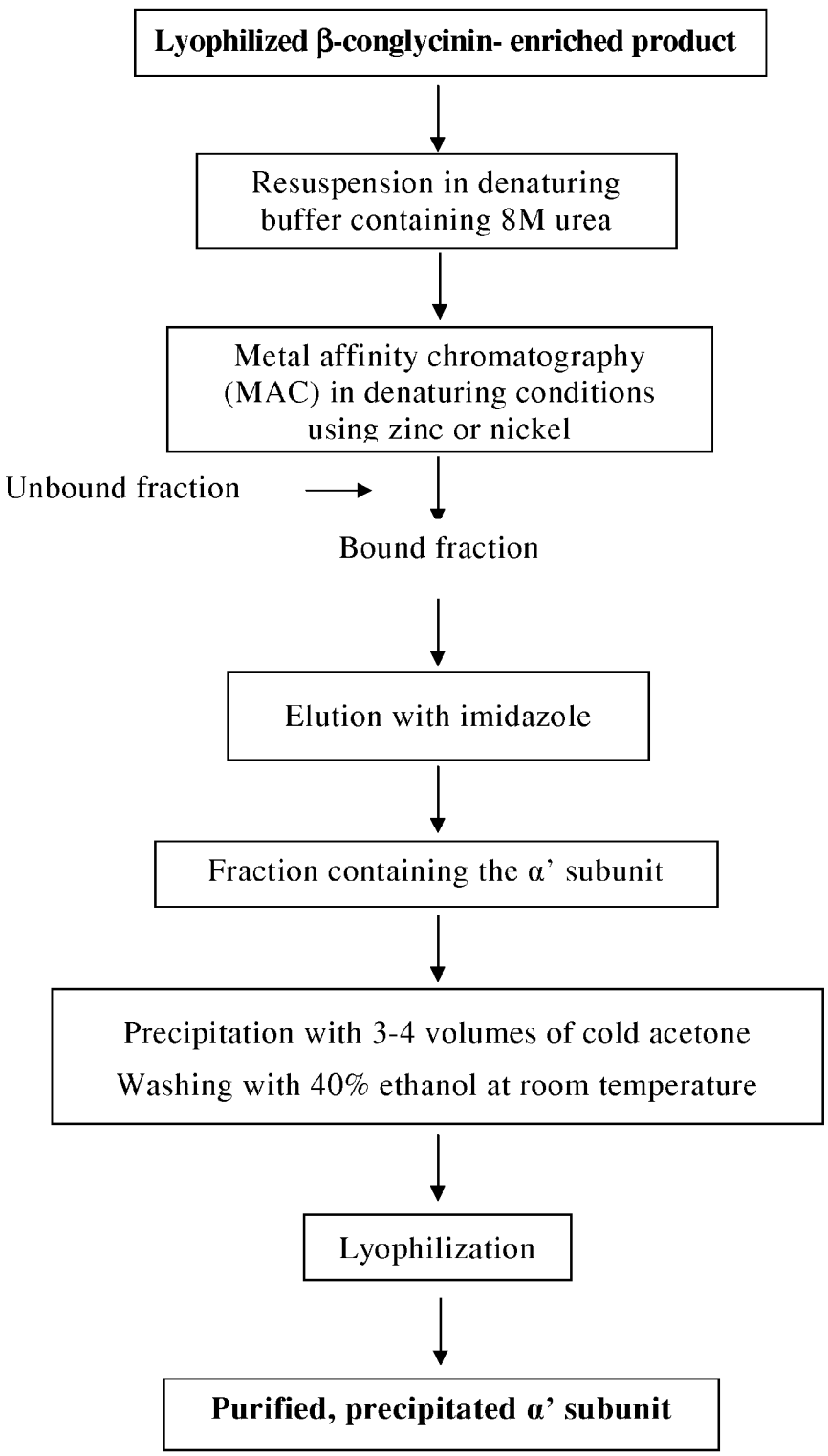
FIG. 2 is a flowchart showing an exemplary process of obtaining purified α' subunit from lyophilized β-conglycinin-enriched product.

Under these pH and temperature conditions, glycinins solubility is very low, therefore these precipitate together with other insoluble material. The precipitate is separated by centrifugation and the soluble fraction is treated with 35-60% (vol/vol) aqueous ethanol, preferably 40% aqueous ethanol, at temperatures ranging from 20 to 30° C., preferably at room temperature, 25° C. The supernatant is centrifuged off and the precipitate, mainly consisting of β-conglycinin, is freeze-dried. The resulting powder is subjected to the subsequent step (FIG. 2).

The choice to separate and purify the α' subunit by means of MAC (Ostrove and Weiss, 1990) depends on its ability to coordinate metal ions such as $Zn^{2+}$ and $Ni^{2+}$, as this subunit has higher histidine content than the α and β subunits (Thanh and Shibasaki, 1978).

A matrix conjugated with zinc or nickel, preferably zinc, is used. According to a preferred embodiment of the invention, the matrix consists of iminodiacetic acid-agarose. The freeze-dried protein material is suspended in a denaturing buffer consisting of 50 mM Tris, 0.5 M NaCl, pH 7.2 and containing 5 to 8 M urea, preferably 5 M. In these conditions, the α' subunit selectively binds to the matrix, and the α and β subunits can be removed by elution with the above buffer; the α' subunit is subsequently eluted with 0.1 M imidazole in the same buffer or in distilled water.

The protein fraction enriched in α' subunit is collected and treated with organic solvents which precipitate the proteins, preferably with cold acetone. Acetone is used in a volume ranging from 2 to 5 times the fraction volume, preferably 3 to 4 volumes, at a temperature ranging between −10 and −30° C., preferably between −15 and −25° C. According to a preferred embodiment of the invention, 3 volumes of acetone at −20° C. are used. The resulting precipitate is separated by centrifugation, resuspended in ethanol, preferably 95% ethanol, further centrifuged and freeze-dried. The lyophilizate contains 94% of protein material and is 10 times more enriched in the α' subunit than the starting material.

Table 1 shows the extraction yields in β-conglycinin and α' subunit from soy flour.

TABLE 1

| Protein fraction | Starting material | Extraction yield (% by weight) |
|---|---|---|
| β-Conglycinin | Defatted flour | 18.7 |
| α' Subunit | β-Conglycinin | 11.0 |
| α' Subunit | Defatted flour | 2.1 |

Polypeptide fragments of the α' subunit are prepared by subjecting the lyophilizate from the previous step to enzymatic treatment with a proteolytic enzyme. According to a preferred embodiment of the invention, the proteolytic enzyme is chymotrypsin and the resulting fragment mainly consists of the amino-terminal region having MW 28,000 Da.

The procedure is as follows: the lyophilizate from the previous step is dissolved at a concentration of 5 mg/ml in 0.2 M $NH_4HCO_3$ containing 1.6 M urea at pH ranging from 7.5 to 8.5. Chymotrypsin is added in a 1:10 to 1:50 ratio, preferably 1:25 w/w to the substrate, incubating at 37° C. with stirring for 24 hours. A step on MAC is subsequently carried out, as described above.

The material eluted with imidazole contains three polypeptide fragments, the main having MW 28,000 Da, and constituting the N-terminal region of the α' subunit.

The administration of the α' subunit and of chymotrypsin fragment to rats (table 2) proved that both are capable of remarkably decreasing cholesterol and total triglycerids plasma levels. In particular, the chymotrypsin fragment proved not only more effective than the other soy components, but also than clofibrate, in reducing cholesterol levels, and it afforded comparable results on triglycerids.

The results of the biological experimentation suggest that the products obtainable according to the process of the present invention, in particular the α' subunit and the fragments thereof, can be used as medicaments, in particular for the treatment of those pathologies which require lowering of cholesterol and/or triglycerids plasma levels. Said compounds will be used, alone or in combination with other active principles and in admixture with suitable carriers, for the preparation of pharmaceutical compositions, in particular for the treatment of hyperlipidemias. Furthermore, they can also be used for the preparation of supplements or food products for dietary regimens to be followed in the above mentioned conditions.

EXAMPLES

First Step: Purification of 7S Globulin from Soy

The starting material was ground soy, defatted according to the Soxhlet method, using pentane as solvent.

Proteins were extracted with a 0.98 g/L $NaHSO_3$ solution in amounts 15 times the volume of the defatted ground soy, for 16 hours at temperatures ranging from 0 to 4° C., keeping pH at 6.4. After centrifugation, the supernatant was treated with 40% ethanol (vol/vol) at room temperature. The resulting precipitate, enriched in β-conglycinin and containing the α' subunit at a double concentration than the starting material, was freeze-dried.

Second Step: Purification of the α' Subunit

The β-conglycinin enriched fraction was resuspended in denaturing buffer (50 mM Tris, 0.5 M NaCl, pH 7.2) containing 5 M urea and purified by MAC on an agarose-iminodiacetic acid matrix (Sigma) conjugated with zinc. The unbound protein material was eluted with the same buffer as above, whereas the bound protein material, mainly consisting of the α' subunit, was eluted with 0.1 M imidazole in the same buffer or in distilled water.

The α' subunit-enriched fractions were treated with 3-4 volumes of acetone at −20° C.; the resulting precipitate was suspended in 40% ethanol at room temperature, then centrifuged and freeze-dried. The resulting powder contains 94% of proteins and is 10 times more enriched in α' subunit than the starting material.

Third Step: Enzymatic Treatment of the α' Subunit

The lyophilizate from the above step was dissolved at a concentration of 5 mg/ml in 0.2 M $NH_4HCO_3$ containing 1.6 M urea, at pH ranging from 7.5 to 8.5. The solution was then treated with chymotrypsin in a 1:25 w/w ratio to the protein substrate and incubated at 37° C. with stirring for 24 hours, then purified by MAC as described above. The material retained by the resin and eluted with 0.1 M imidazole contains three polypeptide fragments, the major one having molecular weight 28,000 Da and consisting of the N-terminal region of the α' subunit.

Biological Experimentation

Animals

Male rats CD SPF/VAF, weighing 75-100 g, were used. The animals were housed in makrolon cages (4-5 animals per cage) in environment with automatic control of light (12 hour light/12 hour darkness cycles), temperature (21±1° C.) and humidity (60±5%).

Experimental Protocol

After 7 day housing, the animals were randomly divided into seven groups of 20 rats each (Table 2). During 28 days, one group was fed with normal diet (cod. 014RF25C; Mucedola S.r.l., Settimo Milanese, MI, Italy), whereas the others were fed with hypercholesterolemic diet consisting of 1% cholesterol, 0.5% cholic acid and 25% hydrogenated coconut oil (batch 332000, preparation Jan. 9, 2000; Laboratorio Dottori Piccioni, Gessate, MI, Italy), with access to water ad libitum. The diet was given daily (40 g, 09.00 a.m.) and the unconsumed amount was weighed. Treatment was carried out as follows.

| | |
|---|---|
| Group 1 (control): | animals fed with normal diet and treated orally for 28 days with a 0.5% carboxymethylcellulose solution. |
| Group 2: | animals fed with hypercholesterolemic diet and treated orally for 28 days with a 0.5% carboxymethylcellulose solution. |
| Group 3: | animals fed with hypercholesterolemic diet and treated orally for 28 days with clofibrate at a dose of 200 mg/kg. |
| Group 4: | animals fed with hypercholesterolemic diet and treated orally for 28 days with the soy total protein extract (TPE) at a dose of 200 mg/kg. |
| Group 5: | animals fed with hypercholesterolemic diet and treated orally for 28 days with β-conglycinin at a dose of 50 mg/kg. |
| Group 6: | animals fed with hypercholesterolemic diet and treated orally for 28 days with the α' subunit at a dose of 10 mg/kg. |
| Group 7: | animals fed with hypercholesterolemic diet and treated orally for 28 days with the α' subunit chymotrypsin fragment at a dose of 1 mg/kg. |

Total cholesterol and triglycerids plasma levels were measured at the end of the 28 day treatment and after 16 hour fasting. The animals were anaesthetized with ethyl ether and blood was drawn from the inferior vena cava in tubes containing EDTA (1 mg/ml). After centrifugation for 15 min at 4° C. at 3000 rpm, plasma was recovered, frozen and stored at −20° C. until measurements.

Total cholesterol and triglycerids plasma concentrations (reported in Table 2) were determined according to conventional enzymatic assays.

TABLE 2

| TREATMENT | Total cholesterol (mg/dL) | Total triglycerids (mg/dL) |
|---|---|---|
| GROUP 1 | 55.4 ± 3 | 105.1 ± 7.2 |
| GROUP 2 | 284.1 ± 10.3 | 226.9 ± 12.6 |
| GROUP 3 | 191.2 ± 8.0 | 139.1 ± 5.8 |
| GROUP 4 | 236.1 ± 10.2 | 176.9 ± 8.1 |
| GROUP 5 | 196.4 ± 7.6 | 146.7 ± 5.9 |
| GROUP 6 | 182.2 ± 12.1 | 150.1 ± 9.8 |
| GROUP 7 | 175.8 ± 7.9 | 140.3 ± 7.4 |

REFERENCES

Anderson J. W., Bryan M. J., Cook-Newall M-E., 1995 *N. Engl. J. Med.* 333, 276-282.

Kirk E. A., Sutherland P., Wang S. A., Chait A., LeBoeuf R. C., 1998 *Journal of Nutrition.* 128, 954-959.

Lovati M R., Manzoni C., Corsini A., Granata A., Frattini R., Fumagalli R., Sirtori C., 1992 *J. Nutr.* 122, 1971-1978.

Lovati M. R., Manzoni C., Corsini A., Granata A., Fumagalli R., Sirtori C., 1996 *J. Nutr.* 126, 2831-2842.

Manzoni C., Lovati M. R., Gianazza E., Morita Y., Sirtori C., 1998 *J. Agric. Food. Chem.* 46, 2481-2484.

Nagano T., Hirotsuka M., Mori H., Kohyama K., Nishinari K., 1992 *J. Agric. Food Chem.* 40, 941-944.

O'Keefe S. F., Wilson L. A., Resurreccion A. P., Murphy P. A., 1991 *J. Agric. Food. Chem.* 39, 1022-1027.

Ostrove S., Weiss S., 1990 *Methods in Enzimology* 182, 371-379.

Thanh V. H., Okubo K., Shibasaki K., 1975 *Plant Physiol.* 56:19-22.

Thanh V. H., Shibasaki K., 1976 *J. Agric. Food. Chem.* 24, 1117-1121.

Thanh V. H., Shibasaki K., 1978 *J. Agric. Food Chem.* 26, 695-698.

Wu S., Murphy P. A., Johnson L. A., Fratzke A. R., Reuber M. A. 1999 *JAOCS* 76, 285-293.

What is claimed is:

1. A purified amino-terminal polypeptide fragment of soy β-conglycinin α' subunit, said fragment purified by a process comprising the steps of:
    (a) extracting a defatted ground soy with an aqueous solution of sodium bisulfite at slightly acidic pH to obtain a β-conglycinin-enriched soluble protein fraction;
    (b) precipitating the β-conglycinin protein fraction from step (a) by treating with ethanol;
    (c) purifying the precipitated fraction from step (b) by Metal Affinity Chromatography (MAC) under denaturing conditions, to isolate the α' subunit;
    (d) precipitating the α' subunit from step (c) with organic solvents;
    (e) enzymatically treating the α' subunit from step (d) with chymotrypsin for a suitable time to produce enzymatically cleaved polypeptide fragments of the α' subunit;
    (f) purifying the amino-terminal polypeptide fragment of the α' subunit from step (e) by MAC.

2. The purified amino-terminal polypeptide fragment of claim 1, wherein the MAC of step (c) and the MAC of step (f) occurs on an iminodiacetic acid matrix conjugated with zinc.

3. The purified amino-terminal polypeptide fragment of claim 1, wherein the polypeptide fragment has a molecular weight of about 28,000 Da.

4. A medicament comprising the purified amino-terminal polypeptide fragment of claim 1, alone or in combination with other active ingredients, in admixture with pharmaceutically acceptable carriers.

5. A method of preparing a medicament for the treatment of hyperlipidemia, comprising combining the purified amino-terminal polypeptide fragment of claim 1 with a pharmaceutically acceptable carrier.

6. A pharmaceutical composition comprising the purified amino-terminal polypeptide fragment of claim 1, alone or in combination with other active ingredients, in admixture with pharmaceutically acceptable carriers.

7. A supplement or alimentary product comprising the purified amino-terminal polypeptide fragment of claim 1.

* * * * *